United States Patent
Rangarajan et al.

(10) Patent No.: US 6,573,498 B1
(45) Date of Patent: Jun. 3, 2003

(54) ELECTRIC MEASUREMENT OF REFERENCE SAMPLE IN A CD-SEM AND METHOD FOR CALIBRATION

(75) Inventors: Bharath Rangarajan, Santa Clara, CA (US); Bhanwar Singh, Morgan Hill, CA (US); Khoi Phan, San Jose, CA (US); Michael K. Templeton, Atherton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 314 days.

(21) Appl. No.: 09/608,096

(22) Filed: Jun. 30, 2000

(51) Int. Cl.$^7$ ................................................ G01N 23/00
(52) U.S. Cl. ..................... 250/307; 250/306; 250/252.1
(58) Field of Search ................................ 250/306, 307, 250/363.09, 310, 396 R, 397–399, 492.1–492.2, 363.03, 252.1

(56) References Cited

U.S. PATENT DOCUMENTS

| | | | |
|---|---|---|---|
| 4,139,933 A | | 2/1979 | Ballard et al. |
| 4,766,311 A | | 8/1988 | Seiler et al. |
| 4,818,873 A | | 4/1989 | Herriot |
| 5,155,359 A | | 10/1992 | Monahan |
| 5,617,340 A | * | 4/1997 | Cresswell et al. ............ 702/85 |
| 5,684,301 A | * | 11/1997 | Cresswell et al. .......... 250/306 |
| 5,804,460 A | * | 9/1998 | Bindell et al. ................ 438/16 |

OTHER PUBLICATIONS

Statistical Methods, George W. Snedecor and William G. Cochran, 1993, Iowa State University Press, 8th edition, p. 149.*

\* cited by examiner

Primary Examiner—John R. Lee
Assistant Examiner—Christopher M. Kalivoda
(74) Attorney, Agent, or Firm—Amin & Turocy, LLP

(57) ABSTRACT

The present invention relates to a system and method for calibrating a scanning electron microscope (SEM). The method comprises measuring an electrical characteristic of a calibration standard reference sample feature and correlating the electrical measurement with an SEM measurement thereof. The correlation of the electrical and SEM measurements provides a critical dimension (CD) for the reference sample feature which can then be used to correlate SEM measurements of workpiece features. The system provides a reference sample having a measurable feature electrically connected to a probe. The probe provides an electrical measurement of the reference sample feature. The system further comprises a scanning electron microscope (SEM) adapted to provide an optical measurement of the reference sample feature. A processor is provided to correlate the optical and electrical measurements of the reference sample feature, whereby a reference feature CD is obtained. The system may further correlate workpiece feature measurements with the reference feature CD in order to determine or obtain a workpiece feature CD.

22 Claims, 8 Drawing Sheets

ELECTRIC MEASUREMENT OF REFERENCE SAMPLE IN A CD-SEM AND METHOD FOR CALIBRATION

TECHNICAL FIELD

The present invention generally relates to semiconductor processing and, more particularly, to a system and method for measuring a sample using a scanning electron microscope and calibration thereof.

BACKGROUND OF THE INVENTION

In the semiconductor industry there is a continuing trend toward higher device densities. To achieve these high densities there have been, and continue to be, efforts toward scaling down the device dimensions on semiconductor wafers. In order to accomplish such a high device packing density, smaller features sizes are required. This may include the width and spacing of interconnecting lines and the surface geometry such as the corners and edges of various features.

The requirement of small features with close spacing between adjacent features requires high resolution photo lithographic processes as well as high resolution inspection and measurement instruments. In general, lithography refers to processes for pattern transfer between various media. It is a technique used for integrated circuit fabrication in which, for example, a silicon wafer is coated uniformly with a radiation-sensitive film (e.g., a photoresist), and an exposing source (such as ultraviolet light, x-rays, or an electron beam) illuminates selected areas of the film surface through an intervening master template (e.g., a mask or reticle) to generate a particular pattern. The exposed pattern on the photoresist film is then developed with a solvent called a developer which makes the exposed pattern either soluble or insoluble depending on the type of photoresist (i.e., positive or negative resist). The soluble portions of the resist are then removed, thus leaving a photoresist mask corresponding to the desired pattern on the silicon wafer for further processing.

In order to control quality in the design and manufacture of high density semiconductor devices, it is necessary to measure critical dimensions (CDs) associated therewith. Semiconductor device features having CDs of interest include, for example, the width of a patterned line, the distance between two lines or devices, and the size of a contact. CDs related to these and other features may be monitored during production and development in order to maintain proper device performance. As device density increases and device sizes decrease, the ability to carry out quick, inexpensive, reliable, accurate, high-resolution, non-destructive measurements of CDs in the semiconductor industry is crucial. The ability to accurately measure particular features of a semiconductor workpiece allows for adjustment of manufacturing processes and design modifications in order to produce better products, reduce defects, etc.

CDs are usually measured during or after lithography. Various operations performed during the lithography process may affect the critical dimensions of a semiconductor device. For example, variations in the thickness of the applied photoresist, lamp intensity during the exposure process, and developer concentration all result in variations of semiconductor line widths. In addition, line width variations may occur whenever a line is in the vicinity of a step (a sudden increase in topography). Such topography-related line width variations may be caused by various factors including differences in the energy transferred to the photoresist at different photoresist thicknesses, light scattering at the edges of the steps, and standing wave effects. Since these factors can greatly affect CDs, fast and reliable monitoring of semiconductor device features is important in order to guarantee acceptable device performance.

Different technologies are currently available to measure CDs associated with semiconductor devices. These include: optical microscopy, stylus profilometry, atomic force microscopy, scanning tunneling microscopy, and scanning electron microscopy. Scanning electron microscopes (SEMs) are commonly used for inspection and metrology in semiconductor manufacturing. The short wavelengths of scanning electron microscopes have several advantages over conventionally used optical microscopes. For example, scanning electron microscopes may achieve resolutions from about 100 to 200 Angstroms, while the resolution of optical microscopes is typically about 2,500 Angstroms. In addition, scanning electron microscopes provide depths of field several orders of magnitude greater than optical microscopes.

In a typical SEM wafer inspection system, a focused electron beam is scanned from point to point on a specimen surface in a rectangular raster pattern. Accelerating voltage, beam current and spot diameter may be optimized according to specific applications and specimen compositions. As the scanning electron beam contacts the surface of a specimen, backscattered and/or secondary electrons are emitted from the specimen surface. Semiconductor inspection, analysis and metrology is performed by detecting these secondary electrons. A point by point visual representation of the specimen may be obtained on a CRT screen or other display device as the electron beam controllably scans a specimen.

Scanning electron microscopes (SEMs) operate by creating a beam of electrons accelerated to energies up to several thousand electron volts. The electron beam is focused to a small diameter and scanned across a CD or feature of interest in the scanned specimen. When the electron beam strikes the surface of the specimen, low energy secondary electrons are emitted. The yield of secondary electrons depends on various factors including the work function of the material, the topography of the sample, the curvature of the surface, and the like. These secondary electrons can be employed to distinguish between different materials on a specimen surface since different materials may have significantly different work functions.

Topographic features also affect the yield of secondary electrons. Consequently, changes in height along a specimen surface may be measured using an SEM. Electron current resulting from the surface-emitted secondary electrons is detected and used to control the intensity of pixels on a monitor or other display device connected to the SEM. An image of the specimen may be created by synchronously scanning the electron beam and the display device.

Although SEMs can achieve resolution in the range of angstroms, calibration is difficult. For example, the magnification of an SEM may be calibrated by placing a sample of known dimensions, such as a chip or wafer having a conductor line of known width, in the instrument and measuring the dimension of the sample. The magnification of the SEM is determined by dividing the SEM measurement of the image of the sample by the known dimension of the sample. The magnification calibration information may then be used to construct a calibration curve, or the SEM's magnification controls may be trimmed accordingly.

Calibration according to these prior methods requires samples of known dimensions. The actual dimensions of a sample, however, may not be precisely known, or may change. In particular, repeated usage of a single reference sample as a calibration standard results in degradation of the reference sample. Charge buildup on a reference sample caused by repeated measurement in a SEM affects the secondary electron emission. Contaminant deposition or buildup also has deleterious effects on measurement of a calibration standard reference sample over time. Conventional SEM calibration methods and systems do not account for the errors in estimating the actual size of a reference feature, and also fail to account for degradation in reference features.

The measurement of a calibration standard reference sample typically involves determining where an edge of the sample is. At the sub-micron range, an edge of a sample may be a complex waveform, as opposed to a flat line. Therefore, in measuring the sample there is uncertainty as to edge location. Where the calibration involves determining the length of a sample, two edges must be located, and thus the edge determination uncertainty increases. Further, sample dimensions may vary as a function of temperature, repeated measurements and electron beam charging causing contamination. The SEM electron beam may thus cause expansion of a reference sample after repeated use. Typically, sample charging during e-beam exposure or material degradation will broaden or change the secondary electron signal.

In order to reduce edge determination error, SEM calibration has also been done using a sample having a series of equally spaced lines. Such a sample could be a diffraction grating having a plurality of aligned parallel grooves. The SEM is used to measure the pitch of the lines. While this method reduces some of the edge quantification errors associated with other SEM calibration methods, higher accuracy calibration methods are needed for SEMs used for measuring high density semiconductor devices.

Conventional SEM calibration methods and systems do not account for degradation of a calibration standard reference sample over time. For example, where a line width feature on a reference sample has a known width, repeated scanning of the feature by an SEM results in charge buildup. This reduces or hampers the ability of an SEM to obtain accurate measurements of the line width in the future. Contamination on a reference sample feature also prevents or hampers accurate readings. Because conventional SEM calibration methods and systems rely upon accurate SEM readings of a known reference feature dimension, inaccurate SEM readings of a calibration standard reference feature cause errors in measurements of workpiece features performed with the SEM. Inaccurate readings may lead to unnecessary rework of a product lot thereby increasing cost.

SUMMARY OF THE INVENTION

The present invention provides a method and system for calibrating a scanning electron microscope, which minimizes or reduces disadvantages associated with conventional methods and systems. In accordance with one aspect of the present invention, there is provided a method for calibrating an SEM using an electrical measurement of a reference sample dimension. A feature, such as for example a conductor line on a reference sample, is measured electrically and measured using a SEM. The electrical and SEM measurements are correlated to determine a critical dimension (CD) for the reference sample feature. A workpiece feature is measured using the SEM, and the reference sample feature CD is correlated with the workpiece feature measurement in order to obtain a workpiece feature CD.

Because electrical measurement is unaffected, or affected differently, by charge buildup and/or other degradation effects on the reference sample, the correlation between the electrical and SEM reference sample measurements can eliminate or reduce the effects of this degradation on system measurements of workpiece features. The electrical reference sample measurement, moreover, may provide trending information relating to degradation of the reference sample over time, as well as an indication of the actual size of a reference feature. In one application of the method, a reference sample is measured electrically, and then optically using a SEM. Thereafter, a workpiece feature is measured, and a workpiece feature CD is obtained using the measurements of the reference sample for correlation.

In accordance with another aspect of the present invention, there is provided a system for calibrating an SEM. The system comprises a reference sample with electrical connections to a probe for measuring a reference sample feature. The system SEM provides an optical measurement of the reference sample feature and correlates the optical and electrical measurements of the reference sample feature to obtain a reference feature CD. The calibration system accounts for degradation in a reference sample associated with repeated usage in a SEM, and further allows trending analysis of the reference sample degradation. Further, the system provides for reduction in the errors associated with initial estimates of the actual reference sample feature size, via an electrical measurement of the feature. Another aspect of the invention provides means for correlating the reference feature CD with a workpiece feature measurement, whereby a workpiece feature CD is obtained.

To the accomplishment of the foregoing and related ends, the invention, then, comprises the features hereinafter fully described and particularly pointed out in the claims. The following description and the annexed drawings set forth in detail certain illustrative examples of the invention. These examples are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 6b is a sectional side elevation view of the exemplary reference sample taken along line 6b—6b of FIG. 6a;

DETAILED DESCRIPTION OF THE INVENTION

Figure 1:
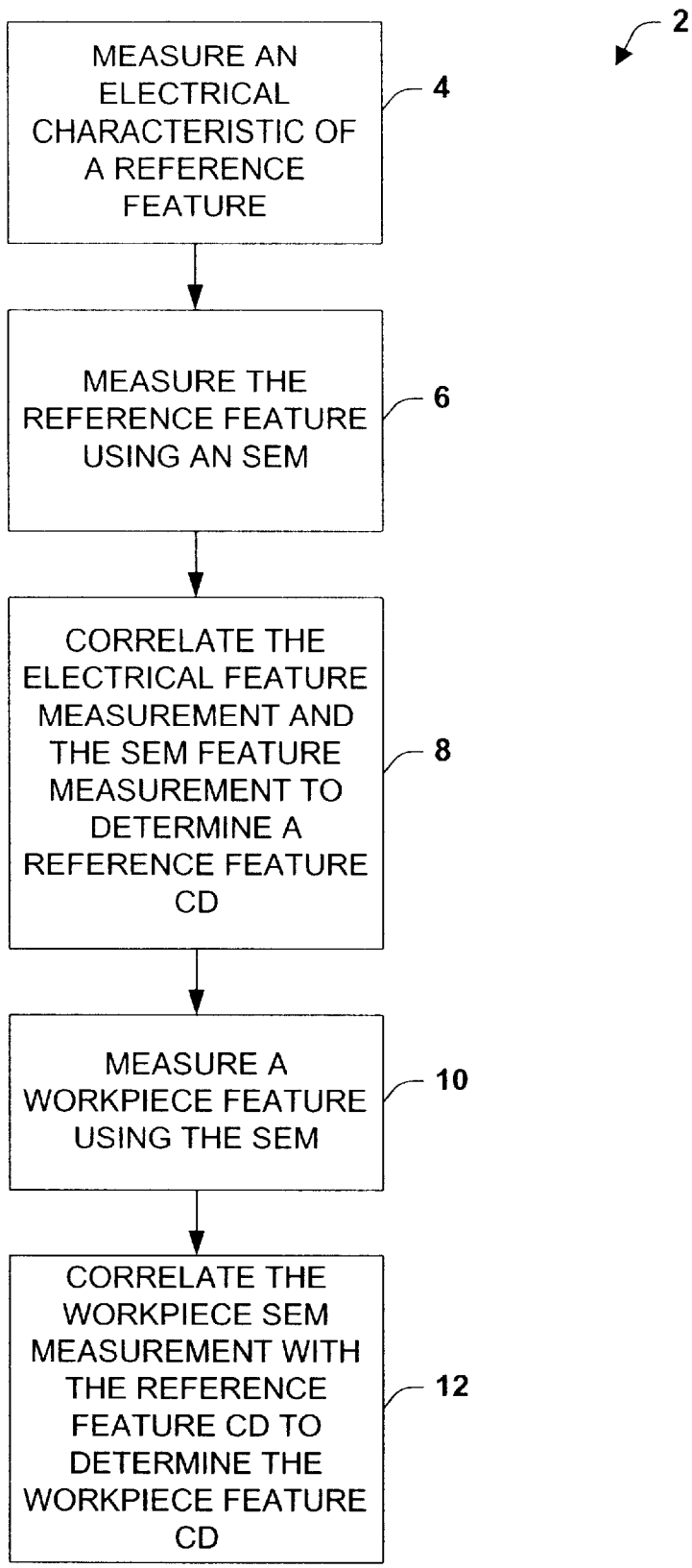
FIG. 1 is a block diagram illustrating a method for calibrating a scanning electron microscope in accordance with the present invention.

The present invention will now be described with reference to the drawings, wherein like reference numerals are used to refer to like elements throughout. FIG. 1 illustrates a method 2 for calibrating a scanning electron microscope. Beginning with step 4, an electron beam is employed on a reference feature to induce a current. At step 6, an electrical characteristic of a reference sample feature is measured, after which an SEM measurement is made of the reference feature at step 8. The electrical and SEM reference feature measurements are correlated at step 10 to obtain a critical dimension (CD) for the reference feature. A feature of interest on a workpiece is then measured at step 12 using the SEM, and a workpiece feature CD is obtained at step 14 by correlating the workpiece SEM measurement with the reference feature CD.

The method of FIG. 1 reduces or eliminates the effects of reference sample degradation on the CD measurement of the workpiece, since the electrical measurement of the reference sample is used to correlate the SEM reference sample measurement. In particular, charge accumulation and contamination deposition associated with repeated usage of a sample in a SEM system, can be accounted for because the electrical measurement of the reference is effected differently by this degradation, than is the SEM measurement thereof. Thus, a user may perform trending analysis to determine the extent of a reference sample's degradation, and calibrate out the effects associated therewith through the correlation of the electrical and SEM reference measurements. The electrical measurement and correlation also eliminate the errors associated with estimating the actual size of a reference feature. Moreover, temperature effects may be accounted for in the correlation of the electrical and optical measurements of the reference feature. The correlation of the electrical and optical (SEM) measurements of a reference sample feature may comprise various mathematical algorithms, such as for example, determining a scaling coefficient, stochastics, neural networks, artificial intelligence, data fusion techniques, and the like.

Figure 2:
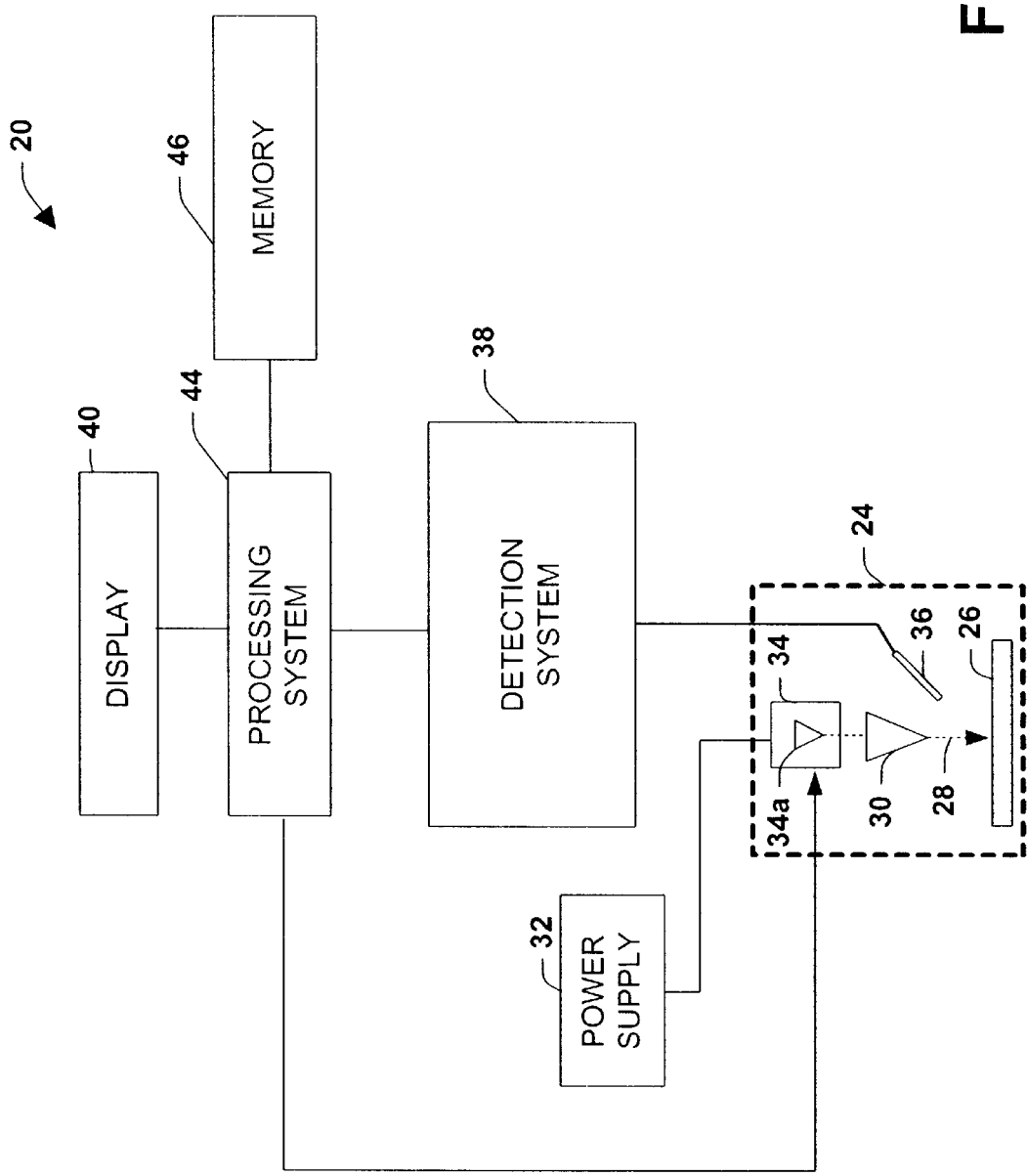
FIG. 2 is a schematic diagram illustrating a conventional scanning electron microscope.

The aspects of the present invention will be further illustrated hereinafter, in comparison with convention methods and systems, which are discussed to provide context for the invention. In particular, FIG. 2 illustrates a CD-SEM system 20 including a chamber 24 for housing a wafer 26. An electron beam 28 is directed from an electromagnetic lens 30 toward the wafer 26. The electron beam 28 is created from high voltage supplied by a power supply 32 associated with a beam generating system 34 which includes an emission element 34a. Various directing, focusing, and scanning elements (not shown) in the beam generating system 34 guide the electron beam 28 from the emission element 34a to the electromagnetic lens 30. The electron beam particles may be accelerated to energies from about 500 eV to 40 Kev.

When the electron beam 28 strikes the surface of the wafer 26, electrons and x-rays are emitted which are detected by a detector 36 and are provided to a detection system 38. The detection system 38 provides detector signals to a processing system 44 for performing conventional critical dimension measurements and signal analysis, for example, to determine the width of a line or other feature of interest on the wafer 26.

Electrons which are emitted from the surface of the wafer 26 which are most useful for critical dimension imaging are known as secondary electrons and provide a substantial amount of the signal current received by the detector 36. A critical dimension image may also be directed to a display 40 by the processing system 44. The processing system 44, in addition to analyzing data received by the detection system 38, synchronizes the scanning of the display 40 with electron beam scanning of the wafer 26 to provide the image. Contrast of the displayed image is related to variations in the flux of electrons arriving at the detector 36 and is related to the yield of emitted electrons from the surface of the wafer 26 to the incident electrons from the electron beam 28.

The detection system 38 receives the electron emissions from the surface of the wafer 26 via the detector 36 and preferably digitizes the information for the processing system 44. In addition, the detection system 38 may also provide filtering or other signal processing of the received signal. The processing system 44 provides critical dimension information to the display 40 and/or stores information in a memory 46.

A processor (not shown) is included in the processing system 44 for controlling the beam generating system 34, providing critical dimension measurements, and for performing signal analysis. It is to be appreciated that a plurality of processors and/or processing systems may be included as part of and/or external to the CD-SEM system 20. The processor in the processing system 44 is programmed to control and operate the various components within the CD-SEM system 20 in order to carry out the various functions associated with the measurement of the wafer 26. The processor may be any of a plurality of processors, such as the AMD Athlon, K6 or other type architecture processors.

A memory 46 is also included in the system 20. The memory 46 is operatively coupled to the processing system 44 and serves to store program code executed by the processor for carrying out operating functions of the system 20 as described herein. The memory 46 also serves as a storage medium for temporarily storing information such as calibration data, critical dimension data, statistical data, and other data. The power supply 32 also provides operating power to the CD-SEM system 20 along with providing a high voltage to the beam generating system 34.

Figure 3:
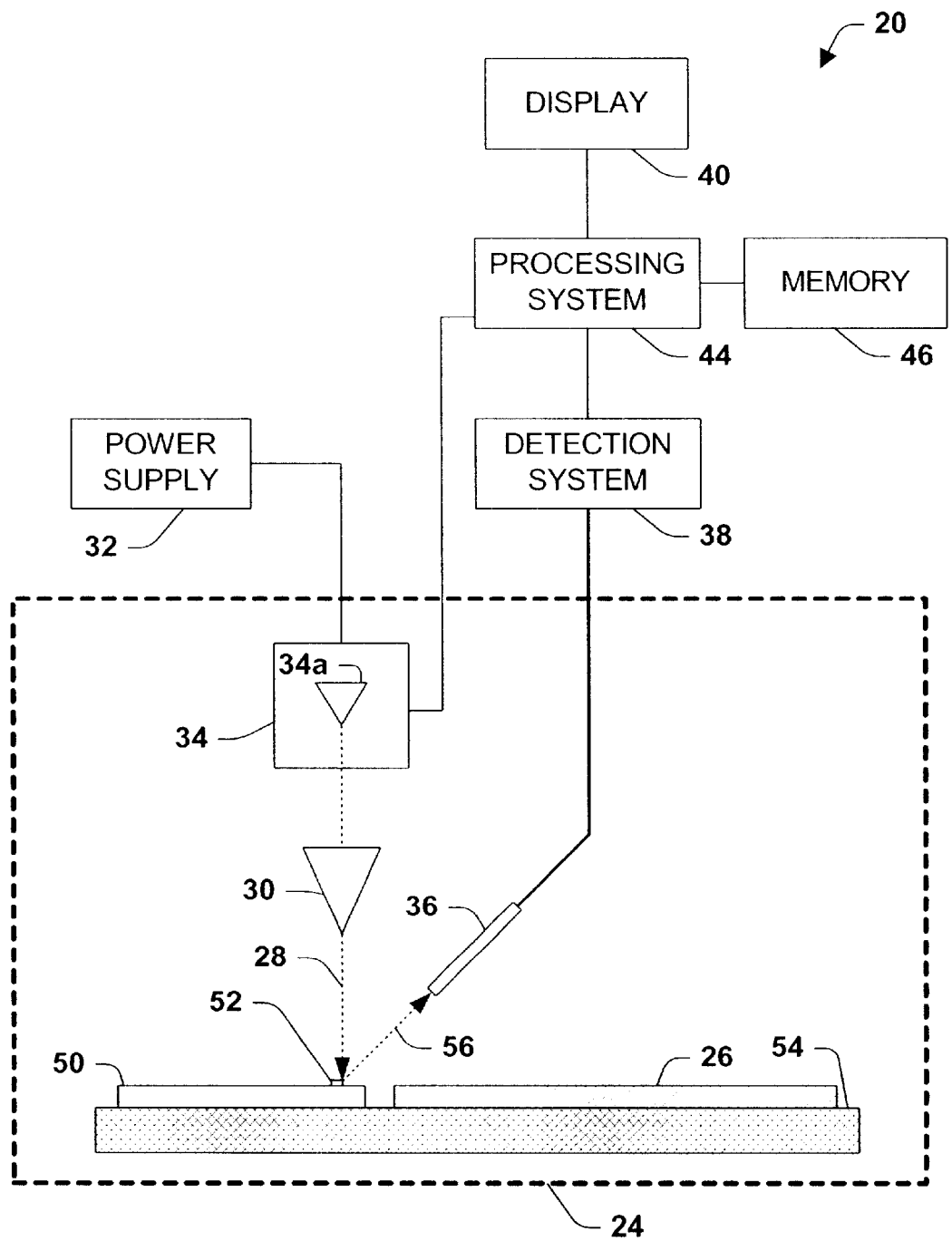
FIG. 3 is a schematic diagram illustrating a conventional system for calibrating a scanning electron microscope.

Referring now to FIG. 3, a conventional SEM calibration is shown, wherein a reference sample 50 having a reference feature 52 is located on a stage 54 and measured by the SEM system 20. The electron beam 28 is directed onto the feature 52, and the detector 36 senses the secondary electrons 56, in order to obtain an optical or SEM measurement of the feature 52 as the stage 54 is displaced relative to the lens 30 in one or more directions perpendicular to the electron beam 28. Where a physical characteristic of the feature 52, such as for example, the width of a conductor line is of interest, the sample 50 may be scanned via movement of the stage 54, whereby a change in the secondary electrons 56 can be determined and a distance (e.g., line width) calculated. Where the line width of the reference feature 52 is known, the reference feature measurement may be used to calibrate the SEM prior to its use in measuring features of a workpiece, such as a semiconductor wafer 26. However, where the dimensions or other characteristics of the reference sample feature 52 changes, due to contamination charge buildup, heat, or other causes, the conventional calibration method of FIG. 3 will not prevent errors in measuring workpiece feature CDs.

Figure 4:
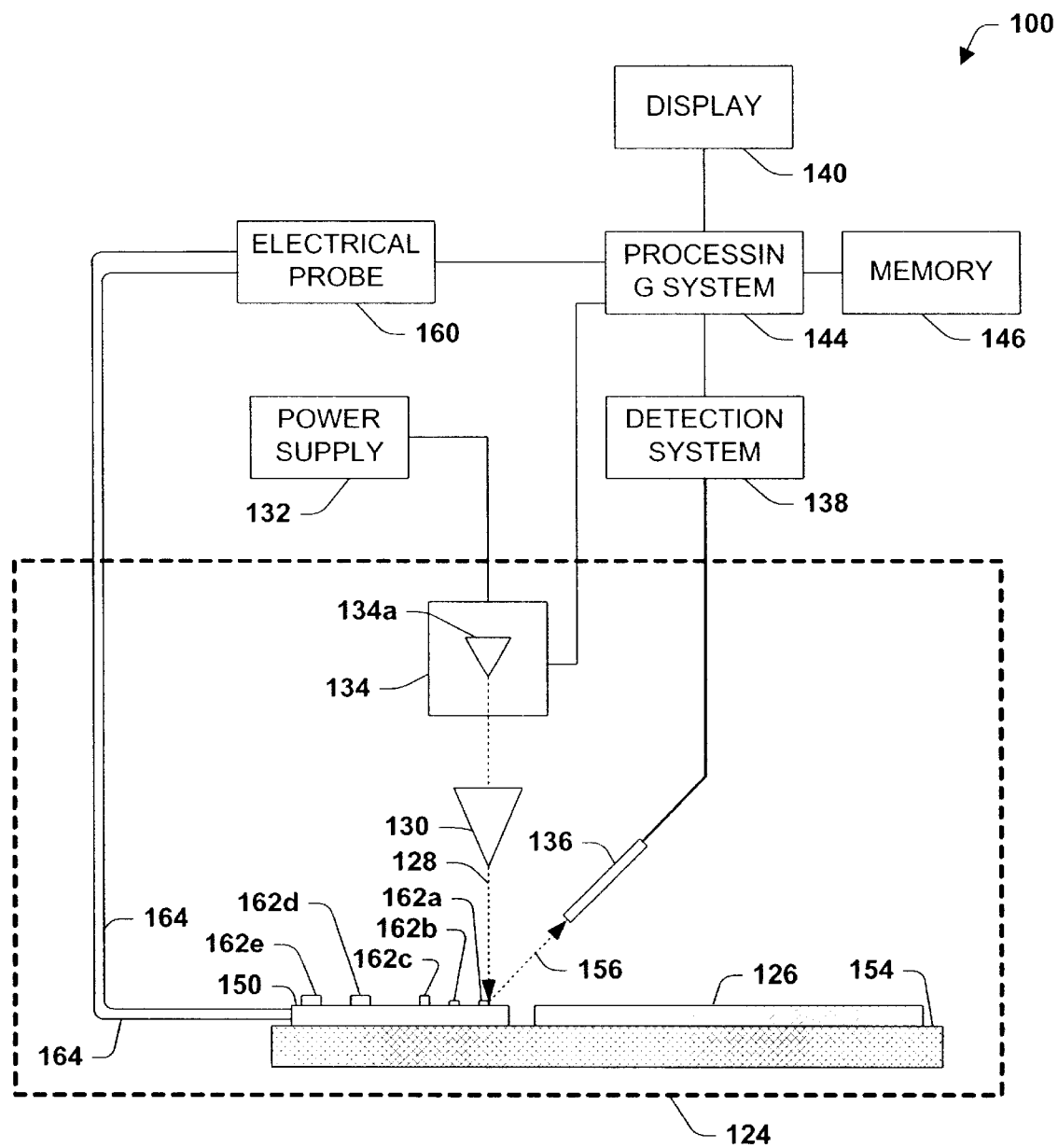
FIG. 4 is a schematic diagram illustrating a system and method for calibrating a scanning electron microscope in accordance with the invention.

Referring now to FIG. 4, a system and method for calibrating a scanning electron microscope are illustrated and described in accordance with the present invention. The system 100 comprises a beam generator 134 having an emission element 134a which provides an electron beam 128 through a lens 130 to a reference sample 150 and/or a workpiece 126, which are mounted on a stage 154, as will be discussed in greater detail infra. Secondary electrons 156 are sensed by a detector 136 which is operatively coupled to a detection system 138. A processing system 144 is provided which receives information from the detecting system 138. The processing system 144 provides critical dimension information to a display 140 and/or stores information in a memory 146. A processor (not shown) is included in the processing system 144 for controlling the beam generating system 134, providing critical dimension measurements, and for performing signal analysis. A plurality of processors and/or processing systems may be included as part of and/or external to the CD-SEM system 100 for performing signal analysis and other operations associated with performing the measurement and calibration methods according to the invention.

The processor in the processing system 144 is programmed to control and operate the various components within the CD-SEM system 100 in order to carry out the various functions described herein. The processor may be any of a plurality of processors, such as the AMD Athlon, K6 or other type architecture processors. The memory 146 is operatively coupled to the processing system 144 and serves to store program code executed by the processor for carrying out operating functions of the system 100 as described herein. The memory 146 also serves as a storage medium for temporarily storing information such as calibration data, critical dimension data, statistical data, and other data which may be employed in carrying out the present invention. The power supply 132 also provides operating power to the CD-SEM system 100 along with providing a high voltage to the beam generating system 134. Any suitable power supply (e.g., linear, switching) may be employed to carry out the present invention.

An electrical probe 160 is connected to the processing system 144 and comprises electrical sensing circuitry or devices (not shown) for measuring an electrical characteristic of one or more features 162a, 162b, etc., (hereinafter referred to as 162) on the reference sample 150 via one or more lead wires 164. The stage 154 is adapted to move horizontally with respect to the vertical electron beam 128 to effect a scanning of the workpiece 126 or reference sample 150 by the beam 128. The probe 160 further comprises an electrical power source (not shown) for energizing the reference sample 150. Thus, the probe 160 may provide a known voltage to the sample 150 via lead wires 164, and measure the resulting current flow, to thereby determine the resistance of one or more features 162 on the reference sample 150. Alternatively, the probe 160 may provide a known current to one or more features 162 of the reference sample 150, and sense the resulting voltage to determine resistance. Many other electrical characteristics of sample features 162 may be measured by the probe 160, such as for example, capacitance, inductance, and the like. Further, although two lead wires 164 are illustrated in FIG. 4, additional wires 164 may be provided as desired to measure electrical characteristics of the reference sample 150 and the features 162 thereon.

In addition to the programs and instructions for carrying out SEM measurements, the processing system 144 is adapted to control the measurement functions of the electrical probe 160 and to receive and analyze data (not shown) from the probe 160 relating to measured electrical characteristics of the reference sample 150. In this regard, the processing system 144 and/or the memory 146 may include programs and instructions for performing various mathematical algorithms, such as for example, stochastics, neural networks, artificial intelligence, data fusion techniques, and the like. These algorithms may be advantageously used to correlate electrical feature measurement data from the probe 160 with SEM measurement data from the detection system 138 in order to calibrate the SEM system 100 as described in greater detail infra. In particular, the processing system 144 may be used to correlate electrical and SEM measurements of one or more reference features in order to obtain or determine a reference feature CD, and to correlate a reference feature CD with a workpiece feature SEM measurement in order to obtain or determine a workpiece feature CD, in accordance with the present invention. The correlation of an electrical and an optical measurement reduces or eliminates prior calibration errors associated with charge buildup, corrosion, and other degradation of a reference sample resulting from repeated usage in a SEM, temperature change, and the like.

According to one aspect of the invention, the probe 160 and lead wires 164 are employed to measure an electrical characteristic of a feature, such as feature 162a, on the reference sample 150. While FIG. 4 illustrates the reference sample 150 as being under the electron beam 128, the electrical characteristic measurement may be performed without the presence of an electron beam 128, for example, with the stage 154 position such that the lens 130 and beam 128 are not above the reference sample, or with the beam generating system 134 de-energized so that no beam 128 is generated.

An electrical characteristic, for example, resistance, of a feature 162a is measured by the probe 160 via lead wires 164. This may be accomplished, for example, by probe 160 providing a known voltage across the lead wires 164, and measuring the resulting current flow, or by injecting a known current into the reference sample 150 and measuring the resulting voltage across the lead wires 164. The stage 154 is then positioned as shown in FIG. 4 and a beam 128 is generated by the beam generating system 134, whereby the system 100 may perform an SEM measurement of the feature 162a. This SEM measurement may be referred to as an optical feature measurement, while the electrical characteristic measurement may be referred to as an electrical feature measurement.

The processing system 144 receives the electrical measurement data or information (not shown) from the electrical probe 160, and receives the SEM optical measurement data or information from the detection system 138. Thereafter, the processing system 144 correlates the electrical and optical measurements of the reference sample feature 162a, via an algorithm such as for example, stochastics, neural networks, artificial intelligence, data fusion techniques, and the like, to obtain a reference sample feature CD (not shown) for the feature 162a. This correlation advantageously provides for calibration of the SEM measurement, and may include compensation for corrosion, charge accumulation, temperature, and other deleterious degradation of a reference sample feature 162. The use of electrical reference feature measurement in conjunction with SEM measurement of the feature 162, therefore, ensures better calibration and accuracy of subsequent SEM measurements of a workpiece feature by virtue of the correlation.

As an example, the electrical reference feature measurement may be a value for the resistance of a conductor line feature 162a on a reference sample 150. Where the length and height of the conductor line and the conductivity of the feature material are known, the resistance measurement may be used to determine the line width of the feature 162a. The SEM optical measurement of the feature 162a may be of the conductor line width. The correlation algorithm may, for example, determine a calibration factor K (not shown), which is the fraction of the electrical reference feature measurement divided by the optical or SEM reference feature measurement. Where, for example, the electrical and optical reference feature measurements were 1.0 and 0.8 microns, respectively, the calibration fraction in this example would be 1.25. Subsequent (or even prior) SEM measurements of workpiece features may be scaled by (e.g., correlated with) the calibration factor K. The invention thus provides for adjustment based on an actual electrical measurement of a reference feature whose dimension may have been estimated in prior systems.

In addition, where the electrical and optical reference feature measurements are taken periodically (e.g., daily, weekly), trending analysis can be performed by the processing system 144, whereby the degradation of a reference sample feature 162 may be determined. As an example, trending may show that the electrical measurement of a reference feature remains fairly constant over a period of time, while the optical measurement of the same reference feature decreases (or increases) over the same timer period. This may be used, for example, to determine that a new reference sample is needed.

In addition to simple trending analysis, the processing system 144 may further perform data fusion analysis, wherein the electrical and optical measurements are analyzed to determine other variables affecting system performance. In this context, data fusion is algorithmic processing of measurement data or information to compensate for the inherent fragmentation of information because a particular phenomena may not be observed directly using a single sensing element. In other words, the data fusion architecture provides a suitable framework to facilitate condensing, combining, evaluating and interpreting the available optical and electrical measurement data or information in the context of the particular application, such as an SEM system 100.

It will be appreciated that the degradation of a reference sample feature 162 will affect the optical and electrical measurements thereof differently, and that the correlation of electrical and optical (SEM) measurements of a reference sample feature 162 provides for improved calibration capabilities within the present invention. Moreover, it will be recognized that many algorithms and correlation techniques are available to compensate for reference sample feature degradation and other errors in the system 100, for example, computing calibration scaling factors, stochastics, neural networks, artificial intelligence, data fusion techniques, mathematical prediction/correction techniques, and the like.

Figure 5:
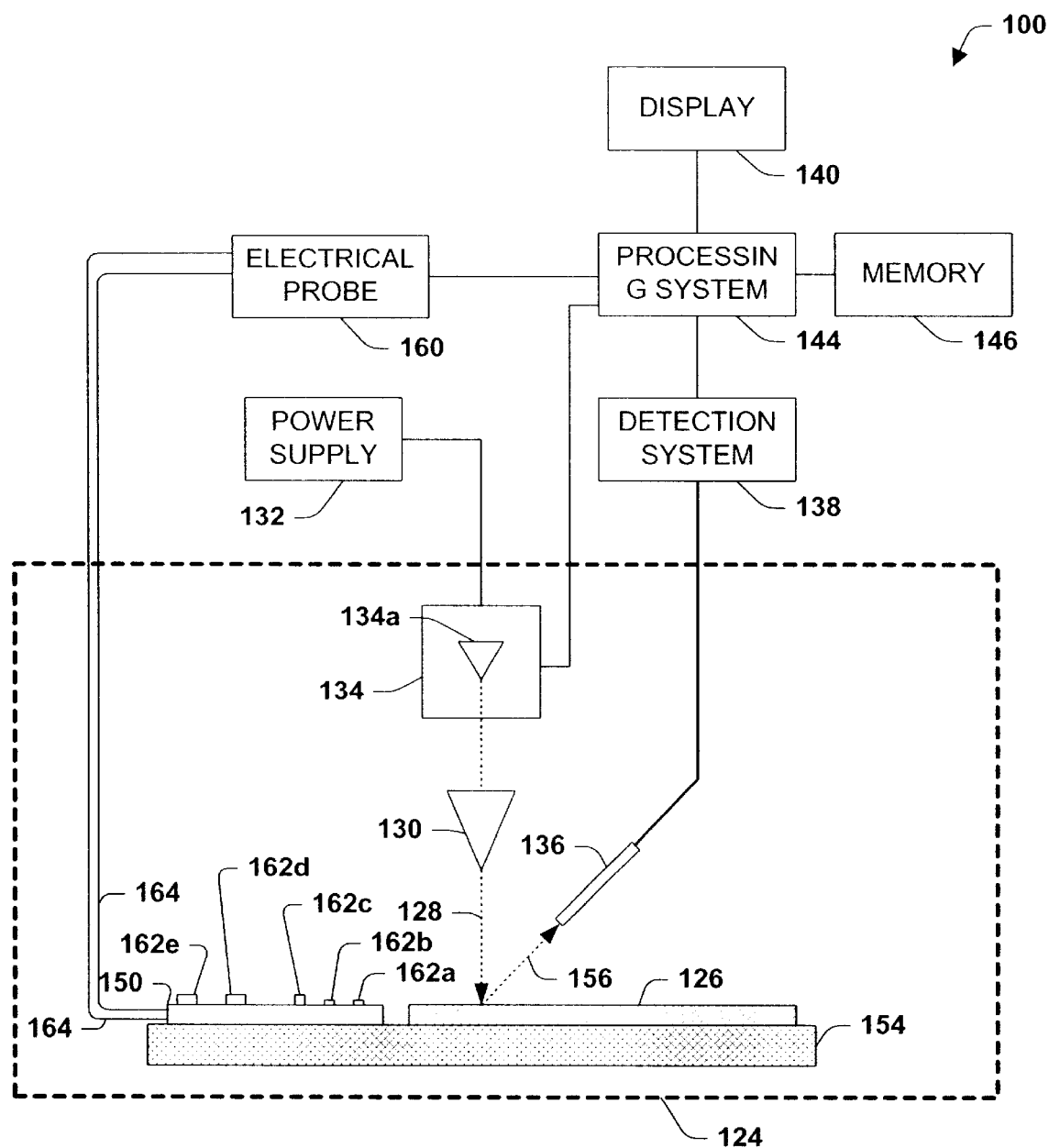
FIG. 5 is a schematic diagram illustrating the system and method for calibrating a scanning electron microscope of FIG. 4.

Referring also to FIG. 5, once the reference feature CD has been obtained or determined, the stage 154 may positioned such that the workpiece 126 is beneath the electron beam 128. Thereafter, the system 100 performs an SEM scan of one or more features of interest (not shown) on the workpiece 126, with workpiece feature measurement data or information being provided to the processing system 144 via the detection system 138. The processing system 144 may then correlate the optical workpiece feature measurement with the reference feature CD in order to obtain or determine a workpiece feature CD. As with the correlation of the optical and electrical reference sample measurements discussed supra, the correlation of the reference feature CD with the SEM or optical workpiece feature measurement by the processing system 144 may comprise, for example, stochastics, neural networks, artificial intelligence, data fusion techniques, mathematical prediction/correction techniques, and the like.

It will be appreciated that the workpiece feature measurement may be performed prior to the reference sample measurements, and further that the reference feature measurements (electrical and optical) may be performed in any order. Furthermore, the measurements need not be performed contemporaneously, since the correlation algorithms and trending analysis may account for the time the various measurements are made. In this way, a workpiece CD may be obtained for a workpiece measured a week prior to the calibration reference feature measurements used to correlate the workpiece measurements, etc.

In the exemplary correlation discussed supra, a calibration factor K was determined from the correlation of the optical and electrical reference feature measurements. In this example, a workpiece feature CD may be obtained by scaling the workpiece feature measurement by the calibration factor K. In this regard, a workpiece feature measurement of 8 microns may be multiplied by the calibration factor K (1.25), to obtain a workpiece feature CD of 10 microns. The system and method of the present invention, thus account for degradation of a reference sample, and calibrate out some or all of the errors caused by this degradation. This was not possible in the prior systems, wherein the reference sample was only measured optically.

Figure 6A:
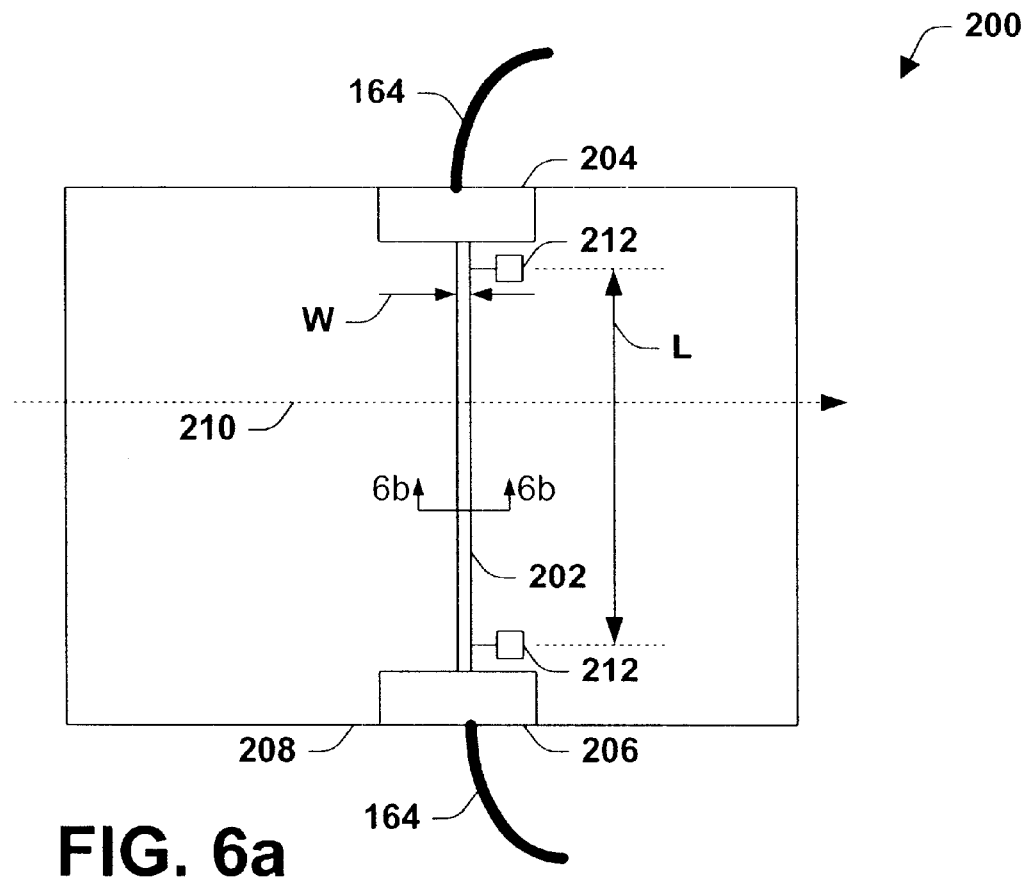
FIG. 6a is a plan view of an exemplary reference sample which may be used in the methods and systems of the present invention.
Figure 6B:
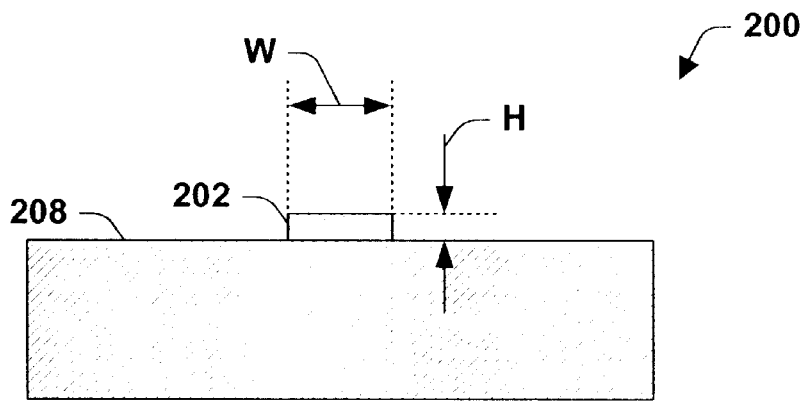

Referring also to FIGS. 6a and 6b, an exemplary reference sample 200 is illustrated, having lead wires 164 for electrical connection with an electrical probe 160 as illustrated in FIGS. 4 and 5. The reference sample 200 comprises a conductor line reference feature 202 extending between connection points 204 and 206 on a substrate 208, and having a width W and a height H. The reference feature line 202 extends a length L between two measurement pads 212. In electrically measuring the reference feature 202, a known voltage (not shown) may be applied by the probe 160 across the length L of the feature 202, and the resulting current there through may be measured using lead wires 164. The resistance of the reference feature line 202 may be computed therefrom. Knowing the conductivity of the reference feature line material and the length L and the height H of the reference feature, the line width W may be calculated by the processing system 144. An optical (SEM) measurement may be taken of the line width W along a scan line 210, which can be correlated with the calculated line width (based on the electrical measurement of the feature line 202), to obtain a reference feature CD (not shown) for the feature 202. The reference feature CD may then be used to correlate optical SEM workpiece feature measurements in order to determine workpiece feature CDs.

Figure 7:
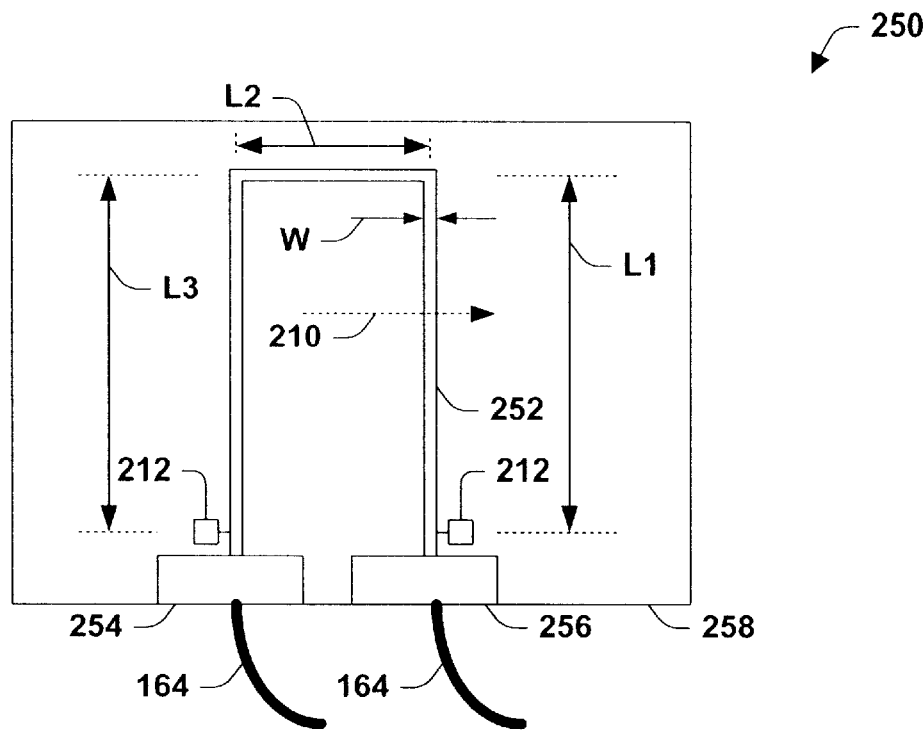
FIG. 7 is a plan view of another exemplary reference sample which may be used in the methods and systems of the present invention.
Figure 8:
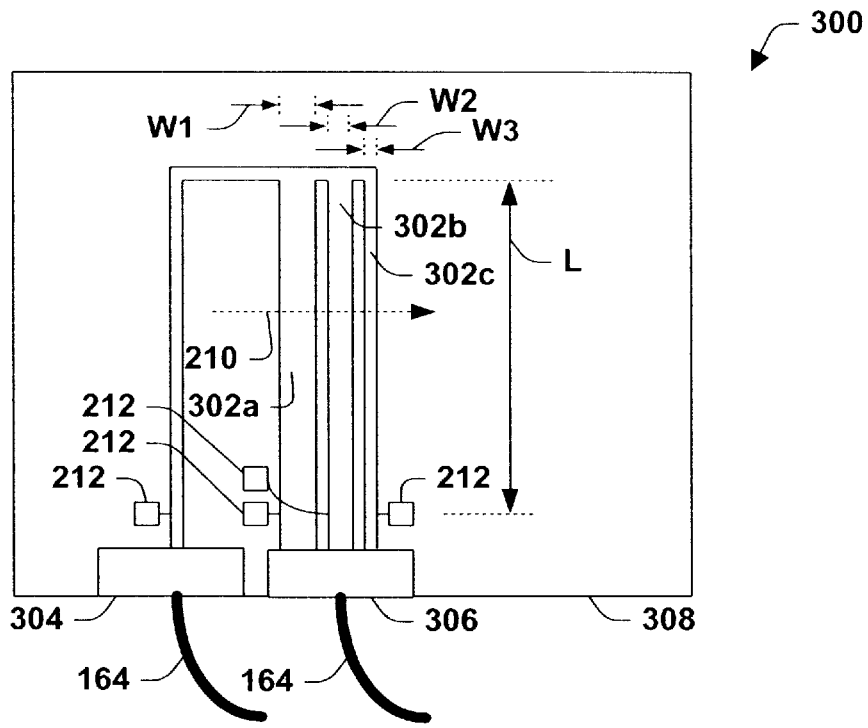
FIG. 8 is a plan view of still another exemplary reference sample which may be used in the methods and systems of the present invention.
Figure 9:
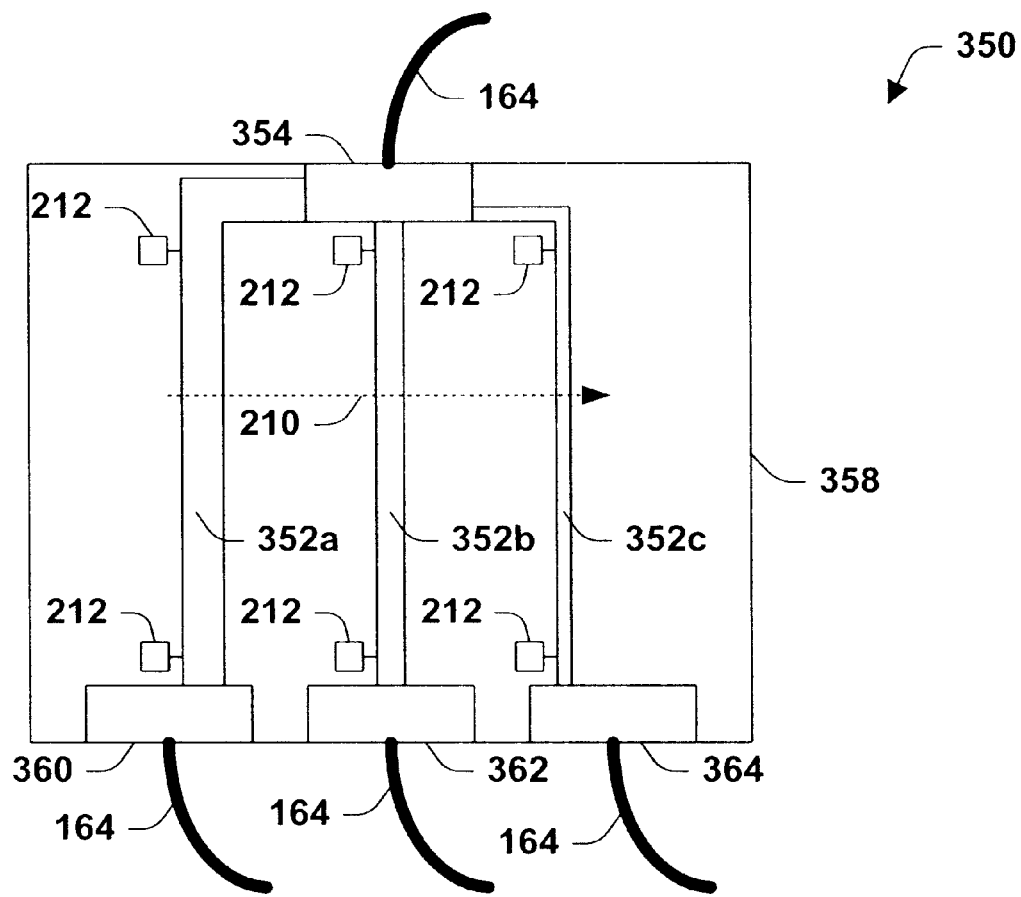
FIG. 9 is a plan view of yet another exemplary reference sample which may be used in the methods and systems of the present invention.

Referring also to FIGS. 7, 8, and 9, other exemplary reference samples 250, 300, and 350, respectively, are illustrated. In FIG. 7, sample 250 has a three section conductor line feature 252, having lengths L1, L2, and L3, respectively. Connectors 254 and 256 are provided on the same side of the sample 250 for connection to a probe 160 using lead wires 164. Additional measurement pads 212 are provided, for example, to provide voltage measurement connections to the sample 250. The reference feature line 252 is fabricated on a substrate 258 of known height and material, to enable a determination of the line width W based on a measurement by a probe 160 of an electrical characteristic of the line 252, such as resistance. This electrical measurement can then be correlated with an SEM measurement along scan line 210 of the width W of the reference feature 252 to obtain a reference feature CD.

In FIG. 8, reference sample 300 comprises several reference features 302a, 302b, and 302c, having widths W1, W2, and W3, respectively on a substrate 308. Each of the reference features 302 can be measured electrically using a probe 160, connectors 304 and 306, measurement pads 212, and lead wires 164, as discussed supra. The electrical measurement can then be used to calculate the width WI, W2, and/or W3 of the reference features 302a, 302b, and 302c, respectively, where the height, conductivity, and length of the conductive paths there through between the connectors 304 and 306 are known. Optical measurements of the reference features 302a, 302b, and/or 302c, taken along a scan line 210 may then be correlated with the electrical measurements thereof to obtain one or more reference feature CDs in the manner discussed above.

Referring now to FIG. 9, a reference sample 350 is illustrated having three reference feature lines 352a, 352b, and 352c of different widths (not shown) on a substrate 358. One common connector 354 and individual connectors 360, 362, and 364 are provided for connection to a probe 160 via lead wires 164. Measurement pads 212 are also provided for connection to individual reference feature lines 352a, 352b, and 352c. Electrical measurements of the reference feature lines 352 can then be correlated with optical SEM measurements taken along a scan line 210 in the manner discussed above. Many different reference samples may be used in the methods and systems of the present invention, and are deemed to be within the scope thereof.

Although the invention has been shown and described with respect to a certain embodiments, it will be appreciated that equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure, which performs the function in the herein illustrated exemplary embodiments of the invention. In this regard, it will also be recognized that the invention includes a system for performing the steps of the various methods of the invention.

In addition, while a particular feature of the invention may have been disclosed with respect to only one of several aspects, such feature may be combined with one or more other features of the other aspects as may be desired and advantageous for any given or particular application. Furthermore, to the extent that the terms "includes", "including", "has", "having", and variants thereof are used in either the detailed description or the claims, these terms are intended to be inclusive in a manner similar to the term "comprising."

What is claimed is:

1. A method for calibrating a scanning electron microscope, comprising the steps of:
    measuring an electrical characteristic of a feature of a reference sample to obtain an electrical reference measurement;
    measuring the feature of the reference sample using an electron beam to obtain an optical reference measurement;
    correlating the optical and electrical reference measurements to obtain a reference sample feature CD;
    measuring a feature of a workpiece using an electron beam to obtain an optical workpiece measurement; and
    correlating the reference sample feature CD and the optical workpiece measurement to obtain a workpiece feature CD.

2. The method of claim 1, wherein correlating the optical and electrical reference measurements comprises executing an algorithm using at least one of a scaling coefficient, stochastics, neural networks, artificial intelligence, data fusion techniques, and trending.

3. The method of claim 2, wherein the reference sample feature is the width of a line, and the electrical characteristic is resistance.

4. The method of claim 3, wherein measuring an electrical characteristic of the feature of the reference sample is before measuring the feature of the reference sample using an electron beam, which is before measuring the feature of the workpiece using an electron beam.

5. The method of claim 1, wherein correlating the reference sample feature CD and the optical workpiece measurement comprises executing an algorithm using at least one of a scaling coefficient, stochastics, neural networks, artificial intelligence, data fusion techniques, and trending.

6. The method of claim 5, wherein the reference sample feature is the width of a line, and the electrical characteristic is resistance.

7. The method of claim 6, wherein measuring an electrical characteristic of the feature of the reference sample is before measuring the feature of the reference sample using an electron beam, which is before measuring the feature of the workpiece using an electron beam.

8. The method of claim 1, wherein the reference sample feature is the width of a line, and the electrical characteristic is resistance.

9. The method of claim 1, wherein measuring an electrical characteristic of the feature of the reference sample is before measuring the feature of the reference sample using an electron beam, which is before measuring the feature of the workpiece using an electron beam.

10. A method for calibrating a scanning electron microscope, comprising the steps of:
    measuring an electrical characteristic of a feature of a reference sample to obtain an electrical reference measurement;
    measuring the feature of the reference sample using an electron beam to obtain an optical reference measurement;
    correlating the optical and electrical reference measurements to obtain a reference sample feature CD; and
    correlating the reference sample feature CD with an optical workpiece measurement to obtain a workpiece feature CD.

11. A system for calibrating a scanning electron microscope, comprising:
    means for measuring an electrical characteristic of a feature of a reference sample to obtain an electrical reference measurement;
    means for measuring the feature of the reference sample using an electron beam to obtain an optical reference measurement;
    means for correlating the optical and electrical reference measurements to obtain a reference sample feature CD;

means for measuring a feature of a workpiece using an electron beam to obtain an optical workpiece measurement; and means for correlating the reference sample feature CD and the optical workpiece measurement to obtain a workpiece feature CD.

12. The system of claim 11, wherein the means for measuring an electrical characteristic comprises an electrical probe in electrical communication with the reference sample.

13. The system of claim 12, wherein the electrical probe comprises a current source adapted to provide a known current to the reference sample, and a voltage sensor for detecting the voltage across the reference sample.

14. The system of claim 13, wherein the electrical characteristic of the feature of the reference sample is resistance.

15. The system of claim 12, wherein the electrical probe comprises a voltage source adapted to provide a known voltage across the reference sample, and a current sensor for detecting the current through the reference sample.

16. The system of claim 15, wherein the electrical characteristic of the feature of the reference sample is resistance.

17. A system for calibrating a scanning electron microscope, comprising:

a reference sample having a reference sample feature;

a probe in electrical communication with the reference sample feature and providing an electrical measurement of the reference sample feature;

a SEM adapted to provide an optical measurement of the reference sample feature; and means for correlating the optical and electrical measurements of the reference sample feature, whereby a reference feature CD is obtained.

18. The system of claim 17, further comprising means for correlating the reference feature CD with a workpiece feature measurement, whereby a workpiece feature CD is obtained.

19. The system of claim 18, wherein the means for correlating the reference feature CD with a workpiece feature measurement comprises a processor adapted to execute at least one of a scaling coefficient, stochastics, neural networks, artificial intelligence, data fusion techniques, and trending.

20. The system of claim 19, wherein the electrical measurement of the feature of the reference sample is resistance.

21. The system of claim 20, wherein the probe comprises a voltage source adapted to provide a known voltage across the reference sample feature, and a current sensor for detecting the current through the reference sample feature.

22. The system of claim 20, wherein the probe comprises a current source adapted to provide a known current to the reference sample feature, and a voltage sensor for detecting the voltage across the reference sample feature.

* * * * *